(12) United States Patent
Broborg et al.

(10) Patent No.: US 10,426,904 B2
(45) Date of Patent: Oct. 1, 2019

(54) VOLUME REFLECTOR STATUS INDICATOR FOR ANESTHESIA SYSTEM

(71) Applicant: MAQUET CRITICAL CARE AB, Solna (SE)

(72) Inventors: Stefan Broborg, Haninge (SE); Jacob Jansson, Sundbyberg (SE); Hans Bocké, Täby (SE)

(73) Assignee: Maquet Critical Care AB, Solna (SE)

( * ) Notice: Subject to any disclaimer, the term of this patent is extended or adjusted under 35 U.S.C. 154(b) by 1105 days.

(21) Appl. No.: 14/427,716

(22) PCT Filed: Sep. 12, 2013

(86) PCT No.: PCT/EP2013/068963
§ 371 (c)(1),
(2) Date: Mar. 12, 2015

(87) PCT Pub. No.: WO2014/041104
PCT Pub. Date: Mar. 20, 2014

(65) Prior Publication Data
US 2015/0250960 A1 Sep. 10, 2015

Related U.S. Application Data

(60) Provisional application No. 61/700,072, filed on Sep. 12, 2012.

(51) Int. Cl.
*A61M 16/00* (2006.01)
*A61M 16/01* (2006.01)
(Continued)

(52) U.S. Cl.
CPC .... *A61M 16/0003* (2014.02); *A61M 16/0057* (2013.01); *A61M 16/01* (2013.01);
(Continued)

(58) Field of Classification Search
CPC .......... A61M 16/0003; A61M 16/0057; A61M 16/104; A61M 16/12; A61M 16/01;
(Continued)

(56) References Cited

U.S. PATENT DOCUMENTS

| 5,931,160 A | 8/1999 | Gilmore et al. |
| 2003/0135087 A1* | 7/2003 | Hickle ................ G06F 19/3406 600/26 |

(Continued)

FOREIGN PATENT DOCUMENTS

| WO | 98/41267 A1 | 9/1998 |
| WO | 02/26304 A2 | 4/2002 |

(Continued)

*Primary Examiner* — Peter S Vasat
*Assistant Examiner* — Margaret M Luarca
(74) *Attorney, Agent, or Firm* — Fay Kaplun & Marcin, LLP

(57) ABSTRACT

An anesthesia system includes a volume reflector, a breathing circuit, a processing unit, and a display operatively connected to the processing unit. The processing unit is configured to provide a status indicator on the display for gas in the volume reflector, the status indicator including a graphical representation of an extent of a driving gas of the volume reflector and/or a patient gas in the volume reflector, and/or a flow of gas and a direction of the flow in the volume reflector, and/or a waste gas flow out of the volume reflector relative a fresh gas flow in the system, and/or a re-breathing fraction (RBF), and/or a balance between the fresh gas flow and patient uptake and/or leakage of gas from the breathing circuit.

19 Claims, 9 Drawing Sheets

(51) Int. Cl.
*A61M 16/10* (2006.01)
*A61M 16/12* (2006.01)
*A61M 16/08* (2006.01)
*G16H 40/63* (2018.01)
*A61M 16/18* (2006.01)
*A61M 16/22* (2006.01)
*G06F 19/00* (2018.01)
*A61M 16/20* (2006.01)

(52) U.S. Cl.
CPC ...... *A61M 16/0891* (2014.02); *A61M 16/104* (2013.01); *A61M 16/12* (2013.01); *G16H 40/63* (2018.01); *A61M 16/0093* (2014.02); *A61M 16/1015* (2014.02); *A61M 16/18* (2013.01); *A61M 16/208* (2013.01); *A61M 16/22* (2013.01); *A61M 2016/003* (2013.01); *A61M 2016/0027* (2013.01); *A61M 2016/0033* (2013.01); *A61M 2016/1025* (2013.01); *A61M 2016/1035* (2013.01); *A61M 2202/0007* (2013.01); *A61M 2202/0208* (2013.01); *A61M 2202/0241* (2013.01); *A61M 2202/0266* (2013.01); *A61M 2205/15* (2013.01); *A61M 2205/3334* (2013.01); *A61M 2205/3379* (2013.01); *A61M 2205/50* (2013.01); *A61M 2205/502* (2013.01); *A61M 2205/59* (2013.01); *G06F 19/3481* (2013.01)

(58) Field of Classification Search
CPC .......... A61M 16/0891; A61M 16/1015; A61M 16/142; A61M 16/18; A61M 2205/3379; A61M 2205/50; A61M 2205/502; A61M 2016/003; A61M 2016/1025; A61M 2016/1035; A61M 2205/15; A61M 2202/0241; G06F 19/3406
See application file for complete search history.

(56) References Cited

U.S. PATENT DOCUMENTS

| | | | |
|---|---|---|---|
| 2005/0139213 A1* | 6/2005 | Blike | A61B 5/14542 128/205.23 |
| 2009/0293872 A1 | 12/2009 | Bocke | |
| 2009/0301491 A1 | 12/2009 | Masic et al. | |
| 2010/0307490 A1* | 12/2010 | Broborg | A61M 16/009 128/203.12 |
| 2011/0138311 A1* | 6/2011 | Palmer | A61M 16/024 715/771 |
| 2012/0180793 A1* | 7/2012 | Schoepke | A61M 16/01 128/204.22 |

FOREIGN PATENT DOCUMENTS

| | | |
|---|---|---|
| WO | 2010/081914 A1 | 7/2010 |
| WO | 2010/130290 A1 | 11/2010 |

* cited by examiner

VOLUME REFLECTOR STATUS INDICATOR FOR ANESTHESIA SYSTEM

BACKGROUND OF THE INVENTION

Field of the Invention

The present disclosure pertains to breathing apparatuses, in more detail to anesthesia systems, and even more particularly to anesthesia systems with a volume reflector being part of a breathing circuit of the system. The anesthesia system includes a display with a man-machine interface in the form of a graphical user interface.

Description of Related Art

Re-breathing of previously expired breathing gases into a patient is, amongst other, desired of economic and environmental reasons, specifically to reduce waste of gas that could be used for ventilating a patient connected to an anesthesia system. In particular breathing gas including an anesthetic gas, such as nitrous oxide or xenon, and/or loaded with one or more evaporated volatile anesthetic agents, such as halogenated anesthetic agents, is desired to be returned to the patient in a subsequent inhalation.

Re-breathing in an anesthesia system can be achieved in a number of different ways.

A conventional way is to provide a bag in bottle system, in which expired gas is being received in a bellows, so as to be collected during expiration and to be forced back to the patient in the next inspiration by applying a pressure compressing the bellows from the outside thereof. The driving gas compressing the bellows is separated from the breathing gas by the bellow's membrane. In a bag in bottle system, with visible bellows, the user can clearly see, from the filling state and movement of the bellows, if there is sufficient re-breathed gas available for the next inspiration. Breaths that are too deep mean that the bellows empties completely, and the breath is thus limited, which is also apparent to the user.

An alternative is to provide anesthetic reflectors for the reflection of unused anesthetic gas back towards a patient during following expiration.

For instance in U.S. Pat. No. 4,989,597, an anesthetic reflector in form of an exchanger for open separation is disclosed. The exchanger directly interfaces a ventilator to a patient breathing circuit, and comprises an elongate tube having a reflector volume. The reflector volume is at least of a size being larger than an expected tidal volume of a ventilated patient. The open separation of the gases is resulting from the suitable length of the tube. There is no divider in the open tube, such as a filter or membrane, such as in a traditional bag in bottle system, between the separated gas columns of the ventilator and the patient circuit. This arrangement allows using the reflector volume with a driving gas column virtually moving back and forth in the reflector volume. An adjacent patient gas column is thus alternatingly moving out of the patient circuit into the reflector volume during exhalation, and back into the patient circuit from the reflector volume during inspiration.

Recently, anesthesia apparatuses emerged on the market not having a bellows, but a volume reflector (VR). For instance, the FLOW-I® is a high-performance anesthesia system with a VR designed to meet the many ventilatory challenges within anesthesia, as well as to provide inhalation anesthesia. Owing to the design, there is minimal mixing between the exhaled gas and a driving gas, such as oxygen, in the VR. Another example of a VR is for example disclosed in WO 2010/130290, which is incorporated herein in its entirety for all purposes, of the same applicant as the present disclosure.

Compared to a bag in bottle system, ventilation parameters are improved in a VR system as there is for instance no interfering membrane between the driving gas and the patient circuit. Another advantage is that the system can deliver the requested breathing gas even in case of leakage, e.g. at the tracheal tube. The VR cannot be emptied like a "bag-in-bottle" because driving gas can be supplied continuously.

The VR might in some circumstances by some operators be considered a "black box" hidden in an anesthesia machine. Hence, there is a need to provide operators of VR based anesthesia systems with means for identifying an operational status of the VR in order to facilitate maneuvering of such an anesthesia system and to fully take advantage of its technical capabilities including very economical operation.

In US patent application US2012/0180793A1 a graphical "bellows simulator" is disclosed. The simulator can show in real time that gas that is conveyed to/from the patient in relation to an adjusted tidal volume. The simulator is provided in form of a simple "bellows-like" animation. The animation disclosed in US2012/0180793 A1 is merely an indicator of ongoing ventilation of a patient illustrating inspiration, expiration and respiratory rate. There is no relation of the disclosure in US2012/0180793A1 to a VR or its function. In addition, a graphical illustration of a bellows is undesired for a system having a VR as it may create user confusion if there is a bellows or VR inside the anesthesia system.

Hence, a more efficient man-machine interface for anesthesia systems having a VR would be advantageous.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing systems, methods, and computer program products according to the appended patent claims.

A status indicator, also referred to as a Volume Reflector Indicator (VRI) herein, is provided according to the disclosure. The VRI includes one or more graphical representations related to the VR filling or operation, fresh gas, inspired gas and/or patient gas. The VRI is preferably displayed on a screen of an anesthesia system with a VR. An anesthesia system with a VR is thus provided, in which the operator is able to follow the course of the ventilation and the operational status of the VR in an easily comprehensible manner. Some of the examples below provide a clearly visible indication of whether a reflector volume is emptying or filling up. Some of the examples allow an operator to see the system is being run economically or uneconomically, e.g. if a fresh gas flow has been turned on which is unnecessarily high for a required anesthetic ventilation.

The "black box" VR hidden in the machine is explained to the operator in an easy to understand manner. The operator is provided with the current function and operative status of the VR. Thanks to this beneficial operative status of a VR graphically presented, the operator may be provided with improved surveillance of the anesthesia system during operation thereof.

The VRI provides a number of advantages, including economical and/or clinical advantages, for instance one or more of the advantages elucidated below, but not limited to these exemplary advantages. Operational safety may thus be improved. Some of the examples of the VRI provide the operator of the anesthesia system for a clarification of how the VR works. Operators are not only provided with a current operational status of a VR, but gain also a deeper understanding of the VR operation and contribution to advantageous patient ventilation, operational safety, and operational economy of the anesthesia system. It is thus possible to reduce the worry of some operators that they can not see a bellows, like in a conventional bag in bottle system, moving up and down and make the user appreciate the advantages of working with a VR instead of such bellows. Hence, a benefit is gained, as a more confident operator of the anesthesia system allows the operator/anesthesiologist to have more, valuable, time for other tasks like caregiving—thanks to the VRI.

Hence, a more efficient man-machine interface for anesthesia systems having a VR is provided in an advantageous manner.

Examples of the present disclosure are aimed at economic use of gas in the anesthesia system, by giving the operator, through graphical indicators of the VR operational status, an intuitive understanding of whether the system is being run economically or not. Metrics may be presented in conjunction with one or more animations of the graphics, which quantifies the economy. It should be noted that the VR status indicator (VRI) of the present disclosure is well superior to a simple metric, which might be difficult to interpret for instance for the status of a VR. The operator is able to understand the graphical representation of the components of the status indicator.

Various aspects of the invention are provided in the appended patent claims. Examples for some specific embodiments are given below.

Some of the examples provide the operator of the anesthesia system for understanding how a breath is limited.

Some of the examples provide the operator of the anesthesia system for understanding how fresh gas is adjusted by the machine in order to supplement breathing if driving gas breaks through into the circle system.

Some examples provide for a penetration of driving gas into the breathing circuit being determinable from the status indicator, e.g. by a drift of a gas front of reflector driving gas towards the breathing circuit. This allows providing an indication to the user, such as by a change of color in a graphical representation of a status indicator, when an adjustment is made which means that the available volume of gas for re-breathing is insufficient without VR penetration or FG increase upon VR penetration.

Some of the examples provide the operator of the anesthesia system for understanding how leaks are compensated for automatically by the anesthesia system.

Some of the examples provide the operator of the anesthesia system with a visualization of the VR activity or status and a current RBF. An indication of the re-breathing fraction (RBF) is provided. The RBF is indicating the balance between fresh gas (FG) and patient uptake, preferably taking into consideration a possible leakage [FG−(leakage+patient uptake)] per breath.

Some of the examples provide the operator of the anesthesia system with an indication that a leakage situation may be present in operation of the system. The operator may then take suitable action if the leakage is deemed too high.

Some of the examples provide the operator of the anesthesia system for an indication of the propagation of the driving gas in the reflector. Preferably, the wave front of the driving gas to the patient gas is indicated.

Some of the examples show the volume leaving the VR during inspiration and the volume returning to the VR during expiration. The volume is shown, for example, with the aid of columns.

Some of the examples facilitate the operator of the anesthesia system to choose efficient fresh gas settings. The operator may choose as low fresh gas flows as possible, while providing the patient with sufficient anesthetic agent, oxygen, etc. Again, advantageous patient ventilation, and operational economy of the anesthesia system are thus maintained.

If the volume returning to the VR is substantially the same as the volume going out of the VR, and no leakage is present, the system is being run economically with no or little patient gas from the expiration, e.g. containing anesthetic gas that one wants to re-use at the next inspiration, leaving the VR during that same expiration to an exhaust of the anesthesia system. If the volume entering the reflector is greater, then it is the difference (gas entering VR minus total reflector volume) that is emptied to the exhaust.

Some of the examples provide the operator of the anesthesia system with an indication for an improved clinical workflow for leakage detection and selection of fresh gas settings.

Patient safety may thus be improved.

Some of the examples of the VRI provide for reduced training of operators needed for operation of the anesthesia system.

DESCRIPTION OF THE PREFERRED EMBODIMENTS

Figure 1:
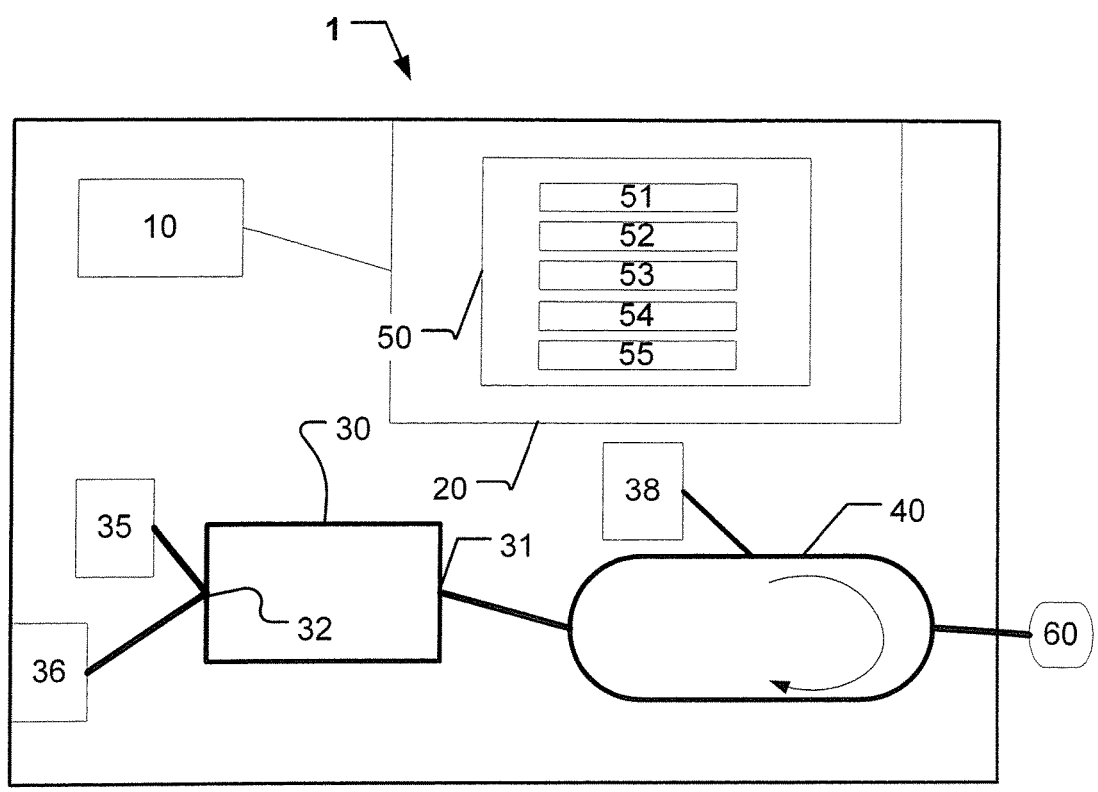
FIG. 1 is a schematic illustration of an anesthesia system with a VR.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

FIG. 1 is a schematic illustration of an anesthesia system 1 with a volume reflector 30. The anesthesia system 1 has the volume reflector 30 connected to a breathing circuit 40. A processing unit 10 is operatively connected to a display 20. The processing unit 10 is configured to provide a status indicator 50, including the aforementioned VRI, on the display 20 for gas in the volume reflector 30. The display 20 of the anesthesia system may be integrated in an anesthesia workstation for ventilating a patient, such as a display or touch screen thereof. The display 20 may also be in communication with such an anesthesia workstation. Communication may be wired or wireless. The display 20 may be a screen of a handheld personal communication device, such as a smartphone, tablet computer, or the like.

The breathing circuit 40 is provided for ventilating a patient 60 with inspiration gas and receiving patient gas during expiration from the patient when connected to the breathing circuit 40. Other components necessary for adequate operation of the system 1, such as controlled inspiratory or expiratory valves, check valves, flow sensors, pressure sensors, amongst others, are not shown or described in the schematic illustration of FIG. 1. Such components are known to the skilled person in the art when reading the present disclosure and apparent when carrying out the present invention. Reference is also made to the description of a more detailed description of the system 1 during inspiration and expiration respectively in FIGS. 4 and 5.

This arrangement allows using the reflector volume with a driving gas column virtually moving back and forth in the reflector volume. Such driving gas column and/or its gas front to patient gas in the VR are graphically provided to the operator according to some examples of the VRI. The reflector volume is cyclically filled with previously exhaled gas, e.g. comprising an anesthetic gas, which is returned to the patient circuit for re-use, i.e. re-breathing, during a subsequent inspiration.

The driving gas of the VR, usually oxygen or air, is used as a driving gas column pushing the patient gas column back into the patient circuit towards the patient during inspiration. Upon the subsequent expiration, the reflector volume is re-filled with expiratory gas and the driving gas column is pushed out of the reflector volume towards EVAC. EVAC is a gas evacuation system usually present in operating theatres and connected to the exhaust of anesthesia machines for taking care of waste gases so as to not letting anesthetic gases escape into the ambient environment.

In this manner an adjacent patient gas column is alternatingly virtually moving out of the patient circuit into the reflector volume during exhalation, and back into the patient circuit from the reflector volume during inspiration.

The volume reflector 30 has preferably a fixed volume, a first port 31, and a second port 32. The breathing circuit 40 is fluidly connected to the first port 31, such that the patient gas is receivable during expiration via the first port 31 while gas in the volume reflector 30 is pushed through the second port as the waste gas flow to an exhaust of the anesthesia system. In this manner a flow of gas is provided in operation of the system 1 from the volume reflector 30 into the breathing circuit 40 during inspiration. Expired gas from a preceding expiration is thus re-breathable by the patient in subsequent inspiration from the volume reflector 30.

A volume reflector, may be designed in various ways in order to provide a well-defined gas front, the channel or tube of the volume reflector is preferably chosen to be narrow. However, this dimension may be weighed against increased flow resistance. Also, compressible volume is chosen to be as low as possible. An adaptation of a volume reflector to different patient categories may be made by varying the channel and/or volume of the reflector. Adaptation of the VR volume may be displayed with the VRI (not shown). Suitable means to vary the reflector volume are disclosed in international patent application WO/2009/062547, of the same applicant as the present application, which is hereby incorporated by reference in its entirety by reference for all purposes.

The system 1 includes a source of driving gas 35 fluidly connected to the second port 32 for pushing the gas from the volume reflector 30 into the breathing circuit during inspiration.

The system 1 includes a source of fresh gas 38 for delivery of a fresh gas flow mixable with the gas pushed from the volume reflector 30 to the patient during inspiration. The source of fresh gas may deliver a desired flow and composition of Oxygen, Air, Nitrous Oxide and vaporized Anesthetic Agents like Halothane, Enflurane, Isoflurane, Sevoflurane, and Desflurane. A re-breathing fraction (RBF) is obtainable as a portion of the re-breathed gas in the inspiration gas delivered to the patient 60. Patient uptake will result in a portion of the Oxygen be consumed and $CO_2$ be part of the expired patient gas. The $CO_2$ is usually removed in a $CO_2$ absorber so that it is not re-breathed. The removed $CO_2$ and consumed $O_2$ are replaced with new Oxygen from the source of fresh gas 38.

The status indicator 50 includes one or more graphical representations related to the VR, fresh gas, inspired gas and/or patient gas. The one or more graphical representations may include a graphical representation 51 of an extent of a driving gas of the volume reflector 30 and/or a patient gas in the volume reflector 30.

Alternatively, or in addition, the one or more graphical representations may include a graphical representation 52 of a flow of gas and a direction of the flow in the volume reflector 30.

Alternatively, or in addition, the one or more graphical representations may include a graphical representation 53 of a waste gas flow out of the volume reflector 30 relative a fresh gas flow in the system 1.

Alternatively, or in addition, the one or more graphical representations may include a graphical representation 54 of a re-breathing fraction (RBF).

Alternatively, or in addition, the one or more graphical representations may include a graphical representation 55 of a balance between the fresh gas flow and patient uptake and/or leakage of gas from the breathing circuit.

The operator may for instance quickly draw conclusions if for instance leakage is present. The operator may also identify at a glance if the system is operated economically or not.

In an example, the operator may quickly identify a high leakage if the system is indicated to be in good balance but is operated at a disadvantageous RBF (waste compensating for leakage and patient uptake by high fresh gas flow). Disadvantageous RBF may be less than the theoretically maximum of approx. 95%. Low RBF's are for instance in the range below 75%, such as below 50% or below 25%. In an example, the operator may quickly identify a system without substantial leakage if the system is indicated to be in good balance and is operated at an advantageous RBF. Advantageous RBF are in the high value range, such as larger than 75% up to the theoretically maximum of approx. 95%.

In another example, if the system is indicated to be out of balance and is operated at a disadvantageous RBF, the system is likely to be operated at an undesired high fresh gas flow leading to a high waste flow out of the system 1. The operator may take suitable adjustments towards more economical operation of the system 1. The status indicator facilitates for an operator of the system to identify an optimization of economical delivery of valuable anesthetic agents to a patient.

Figure 2:
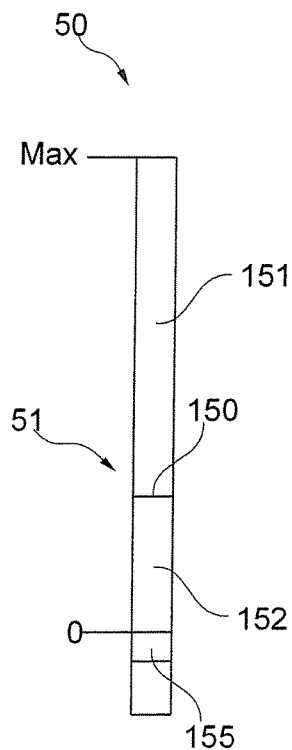
FIG. 2 is a schematic illustration of an example of a volume reflector indicator.

In an anesthetic system with a volume reflector, the patient obtains under all circumstances a sufficient volume of breathing gas, by contrast to a bag in bottle system. However, the driving gas column of a VR may enter the patient circuit during inspiration as there is no membrane between the driving gas and the patient gas. This crossing of the reflector driving gas over the volume reflector, also called break-through or penetration of driving gas through the VR, is an undesired condition, as the patient may receive less anesthetic agent than needed. Driving gas pushed through the volume reflector into the circle system may be conveyed to the patient. It is though an advantage that the patient is ventilated in a VR system also with a penetration of the VR, in contrast to a bag in bottle system where ventilation stops until the user fills the system including the bellows with fresh gas, for example by activating an O2 flush. FIG. 2 is a schematic illustration of an example of a status indicator 50 in form of a VRI. The Indicator includes a graphical representation of a boundary 150 between a driving gas column 151 and patient gas from a preceding expiration 152 that is located in the volume reflector 30.

In an example, the column representing the patient gas column from a preceding expiration 152 can change visual appearance, such as a change of color. For instance when an adjustment is made which means that the volume of patient gas in the volume reflector 30 is an insufficient amount of gas for a subsequent inspiration, the VRI may provide an indication to the user by a color change of the column. For instance, if driving gas penetrates the reflector 30 into the breathing circuit 40, this indication may be made by means of such color change to the operator of the system 1.

It is also conceivable for the anesthesia system 1 to have a mode that automatically compensates for such conditions. In this manner correct patient ventilation and breathing is achieved at all times, for instance by means of a fresh gas flow being increased during inspiration. This type of compensation may be indicated graphically, e.g. as a fresh gas column indicator 155, such as under the driving gas column indicator 151 and patient gas column indicator 152. With this type of presentation, a leakage indicator is thus also obtained. The increased fresh gas flow compensates for patient uptake and leakage. It may be provided to the operator, such as in the example of the status indicator 50 in FIG. 2.

An increased flow of fresh gas can hence be shown to the operator, e.g. with another color, in order to provide an indication of possible leakage. This may be provided in an automatic leakage compensation mode of the system 1.

The operator may adjust the anesthesia system 1 such that a break-through, i.e. the driving gas column 151 entering the breathing circuit 40 during inspiration, is allowed from the volume reflector 30. This too may be presented graphically.

Figure 3A:
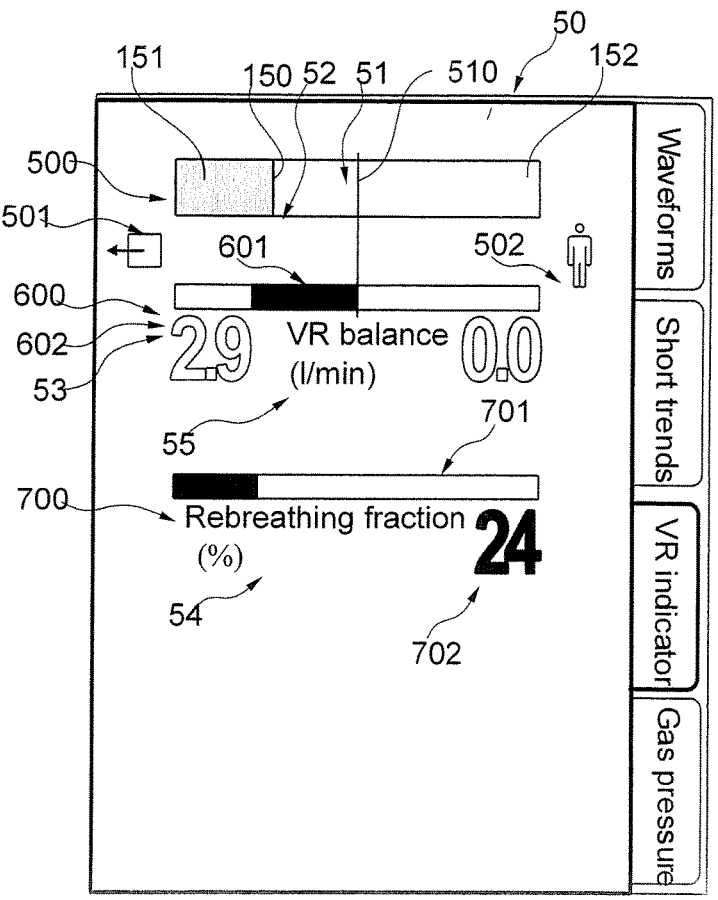
FIGS. 3A and 3B are schematic illustrations of another example of a VRI in two operative examples.
Figure 3B:
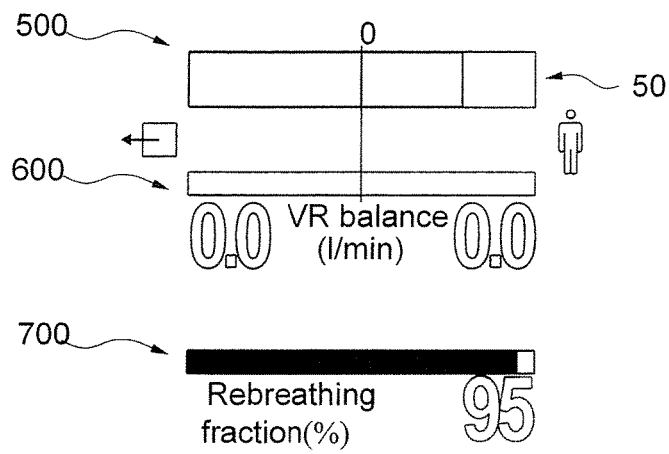

A further example of a status indicator 50, such as a VRI is now elucidated with reference to FIGS. 3A and 3B. The status indicator 50 includes in the example three separate graphical representations for illustrating different aspects of the status indicator 50.

A flow indicator 500 is included in the status indicator 50 for indicating a current flow and its direction in or out of the VR during a breathing cycle. This is a bar graph during a breathing cycle. It includes a graphical representation 52 of a flow of gas and a direction of the flow in the volume reflector 30.

Moreover, a VR balance indicator 600 is included in the status indicator 50. It includes a graphical representation 53 of a waste gas flow out of the volume reflector 30 relative a fresh gas flow in the system 1. Further, the VR balance indicator 600 includes a graphical representation 55 of a balance between the fresh gas flow and patient uptake and/or leakage of gas from the breathing circuit.

Further, a RBF indicator 700 is included in the status indicator 50. This graphical representation includes a graphical representation 54 of a re-breathing fraction (RBF).

These components of the exemplary VRI illustrated in FIG. 3A and B are described in more detail hereinafter.

The status indicator 50, such as illustrated in the examples of FIG. 2 and FIGS. 3A,B is provided without information overload to the operator. This is advantageous in many clinical situations where a quick look informs the operator of the current status of the system 1 as provided by the status indicator 50. The status indicator 50 has moreover excellent readability and quick understanding of a VR status in the system 1.

As the status indicator 50 may have several components (flow indicator 500, balance indicator 600, RBF indicator 700) with various complexities, the operator may choose at its discretion the level of information read from the status indicator 50. For instance, the RBF indicator 700 is quickest to capture by the operator. The balance indicator 600 and the flow indicator 500 provide alternative and/or additional information to the operator at a different level of complexity and might be directed to advanced clinical users providing complex information in an easy to understand format. The example of FIGS. 3A and 3B requires only a screen with low resolution thanks to the absence of images of graphics. This might provide for a less expensive system 1 as suitable display hardware may be chosen accordingly.

The VR balance indicator 600 and/or the RBF indicator 700 may be updated breath-by-breath. Alternatively, or in addition the VR balance indicator 600 and/or the RBF indicator 700 may be provided as a mean value, such as calculated as a mean value from values of a plurality of precedent breathing cycles.

In addition to a status indicator 50, a penetration detector of Reflector Driving Gas into the breathing circuit 40 may be provided to inform the operator of a possible RDG penetration, as described in WO 2010/130290, which is incorporated herein in its entirety for all purposes, of the same applicant as the present disclosure. The status indicator 50 may comprise a graphical representation that RDG penetrates into the breathing circuit.

Now, turning to the components of the exemplary VRI:

a) Flow Indicator 500

The flow indicator 500 is an animation, preferably in real time. The physical volume extension of the Volume reflector is illustrated as a bar graph. At a first end of the bar graph, an exhaust (Evac) symbol 501 for waste gas to a gas evacuation system is provided. The first end corresponds to the second port 32 of the VR. At the other end, a patient symbol 502 for the patient 60 connected to the breathing circuit is given. The second end corresponds to the first port 31 of the VR. The flow indicator 500 is a momentary movement indicator of the gas front during a breathing cycle.

At the start of a breath, the animation starts from the mid-line 510 and goes toward the patient, here to the right towards the patient symbol 502. During inspiration, the bar 151 symbolizing driving gas in the VR moves from the midline 510 towards the patient ->->->. The wave front from the driving gas to the patient gas is illustrated by the end border line 150 of the bar 151. Physically, driving gas is pushed into the VR at the second port from the source of driving gas 35. During expiration, the area 151 symbolizing driving gas reverses to the middle<-<-<-. Patient gas, as symbolized by the area 152 of the bar graph, moves into the VR.

With an ideally adjusted fresh gas (FG) flow, the movement caused by the expiration of the patient stays at the middle line 510. This would provide most economical operation of the system 1.

Under certain operative conditions, with a low FG flow falling below the patient's uptake, and/or a leakage, the bar graph, i.e. the line 150 may stay before/to the right of the mid-line for excessive flows.

In the example illustrated in FIG. 3A, the patient gas continues to move towards the second port 32 of the VR. The area 152 crosses the midline 510. This happens when the FG flow is too high. The two bars illustrating driving gas 151 and patient gas 152, separated by line 150 of the graph, continue to move to the left of the mid-line 510 and runs toward evac/waste 501 and the loss is illustrated. The user can thus easily see that the system is being run uneconomically and can take measures. For example, the user can adjust the FG flow.

Zeroing of the graph may be done at the start of each new inspiration, i.e. at a new inspiration, the graph starts again at the mid-line 510. Each breath is thus illustrated starting from the mid-line 510 and Waste Gas/break-through is calculated for each individual breath.

Without such zeroing of the graph, i.e. without restarting from the mid-line 510 for every breath, the gas front between driving gas and patient gas, illustrated with line 150, reciprocates back and forth for each breathing cycle with a variable end point between each breathing cycle. In this case a drift over time in the gas front may be illustrated.

The flow indicator 500 bar graph may have an amplitude corresponding to the size of the tidal volume of a breath, i.e. a smaller tidal volume results in a smaller amplitude of the bar graph than a larger tidal volume. Alternatively, the flow indicator 500 bar graph may be provided with auto scaling to visualize a broad range of gas flows.

In FIG. 3B, the status indicator 50 of FIG. 3A is illustrated in another operational setting. Reference numerals for like elements are not repeated and reference is made to FIG. 3A. In FIG. 3B the status indicator 50 is shown during inspiration, the driving gas column 151 animation has moved to the right, i.e. towards the breathing circuit 40 pushing patient gas from a preceding expiration 152 into the breathing circuit 40.

This flow indicator 500 may also be applied to visualize a gas drift into or out of a bellows, which otherwise may be difficult to spot for the operator. Overfilling or draining of a bellows may be shown with such a balance indicator 500 in anesthesia systems having a bellows instead of a VR.

b) VR Balance Indicator (l/min) 600

The VR balance indicator 600 includes a graphical representation 53 of a waste gas flow out of the volume reflector 30, toward the Evac symbol 501, relative a fresh gas flow into the breathing circuit 40. Further, the VR balance indicator 600 includes a graphical representation 55 of a balance between the fresh gas flow and patient uptake and/or leakage of gas from the breathing circuit. More precisely, the balance is calculated as (FG−(leakage+patient uptake)). This graph incorporates both leakage and waste gas, i.e. FG flow is too high compared to patient uptake and leakage.

With an ideally adjusted fresh gas (FG) flow, compensation by introduced FG is covering substantially for the patient uptake and leakage. The VR balance indicator bar 601 stays at the middle line 510. This would provide most economical operation of the system 1.

The VR balance indicator is intuitive to understand by the operator. The bar is ideally 0—at most economic operation, no waste is made. The bar of graph 600 is for instance provided in an alerting color, like red, regardless of the bar extending to the right or the left from the mid-line 510. The less the extent of the bar, the better. This balance illustration explains the operational state of the system 1 better to an operator than a leakage number which has to be interpreted by the operator who might has to focus on other clinical operations.

In FIG. 3A, the FG flow is an important part of the minute volume—i.e. the tidal volume and the mid-line 510 is crossed. A flow out from the reflector, i.e. as a Waste Gas corresponding to a conventional "pop off flow" in bag in bottle/bellows systems. The "VRI-flow" is shown in the VR balance indicator 600 in [l/min], in the example shown as metrics in addition to the bar 601.

In FIG. 3B, a balance of the system 1 is illustrated. Neither waste nor leakage are present in this operational condition as can be seen from the "0,0" l/min flow of the balance indicator 600. Alternatively, this may also indicate that waste flow is as large as leakage and compensated by a correspondingly increased FG flow. However in the present example, the RBF is 95% i.e. basically all previously expired patient gas is led back into the patient, which is an indication to the operator that FG flow and thus leakage is low.

By means of the bar indicating an unbalance, the operator can thus easily see that the system 1 is being run uneconomically and can take measures. For example, the user can reduce the FG flow or take measures against leakage, e.g. inflate a cuff of an intubation tube in the patient trachea to be tighter against the trachea.

Other examples, such as illustrated below in FIG. 6, may have two bars for the balance indicator, namely one bar for waste gas flow and a second bar for leakage flow, providing more detail.

c) RBF Indicator (%) 700

Further, a RBF indicator 700 may be included in the status indicator 50. This graphical representation includes a graphical representation 54 of a re-breathing fraction (RBF). RBF is the proportion of expired gas from a preceding expiration that is re-breathed by the patient upon subsequent inspiration and that contains gas from the VR. The RBF may come close to, but in practice never reach, 100% on account of the fact that CO2 is absorbed in a CO2 absorber and is replaced with FG. For example, if one has a Bias Flow or a minimum FG flow, for example 0.3 l/min minimum FG flow, the RBF becomes dependent on the patient's Tidal Volume (TV). A small TV implies a lower RBF, and the higher it is the greater the TV the patient has.

This is made clear to the user from the RBF indicator's 700 visualization.

The RBF is shown in the example of FIG. 3A as 24%.

A graph 701 and/or a metric 702 may be provided for the RBF indicator 700.

In FIG. 3B the RBF is 95% as mentioned above.

Other examples of status indicators 50, are illustrated in FIGS. 6 to 12, and may comprise one or more of
a graphic indication of a flow into the VR,
a graphic indication of a flow out of the VR,
a FG flow indicator, a leakage rate indicator,
a VR gas Flow direction indicator,
a Waste gas volume or flow indication, etc.

A status indicator 50 as described herein may be provided as a decision aid that can help an anesthetist make the desired adjustments for fresh gas and the re-breathing fraction, and it can improve the understanding of how the volume reflector functions together with the whole system.

The indicator 50 can improve the understanding of how the volume reflector functions together presenting a status indicator of the volume reflector and/or breathing circuit on the display.

The system can prompt an operator if a certain operative condition is met, such as too high FG is used as economically necessary, a leakage is present, and/or a penetration of driving gas is present. Several operative conditions may be present and prompted at the same time to the operator.

According to an aspect of the disclosure, a clinical decision support system is hence provided for an anesthesia system. Some examples of the decisions the clinical decision support system allows for are given hereinafter.

An efficiency meter may hence be provided for the anesthesia system 1. The efficiency meter may include a first indicator, such as a bar graph, for a status of the volume reflector including at least one of:
- an extent of a driving gas of the volume reflector 30 and/or a patient gas in the volume reflector 30, and/or
- a flow of gas and a direction of the flow in the volume reflector 30, and/or
- a waste gas flow out of the volume reflector 30 relative a fresh gas flow in the system 1, and/or
- a re-breathing fraction (RBF), and/or
- a balance between the fresh gas flow and patient uptake and/or leakage of gas from the breathing circuit.

Different visual indicators, such as different colors, may give an indication of efficiency of operation of the system 1.

For instance the VR balance indicator 600 may be provided in an alerting color. The bar of graph 600 is for instance provided in an alerting color, like red, regardless of the bar extending to the right or the left from the mid-line 510. The less the extent of the bar, the better the operational efficiency.

The RBF indicator 700 may be provided in a color indicating an acceptable level of operation, such as in green. A bar of the RGF indicator may be given in green and the higher extent the bar has, the more positive is the operational efficiency.

Processing unit 10 might provide for operator selections and adjust settings regarding desired efficiency. Some operator may for instance choose a certain minimum FG flow.

For instance choosing a minimum FG flow of e.g. 0.2 l/min will result in a high RBF value, such as around 95%, when the actual FG flow is at this minimum flow. At lower RBF values, the clinical decision support system may provide for suitable suggestion to the user, e.g. to improve operational efficiency. Choosing a minimum FG flow of a higher value, such as 1.5-2 l/min, will result in a lower RBF value during operation of the system 1, even when the actual FG flow is at this rather high minimum flow. Depending on patient, tidal volume, etc. this chosen lower FG flow limit will result in maximum RBF values lower than in the previous example, such as around 50%, when the actual FG flow is at this minimum flow. In this example, the clinical decision support system may provide for suitable suggestion to the operator, e.g. to improve operational efficiency, at lower RBF values than in the previous example. Thanks to this adjustability, the operator may focus on other clinical tasks without being distracted by an indication for suggestions to make adjustments that in this case are not necessary (due to the selected allowed minimum FG flow requiring a somewhat uneconomical operation).

Figure 4:
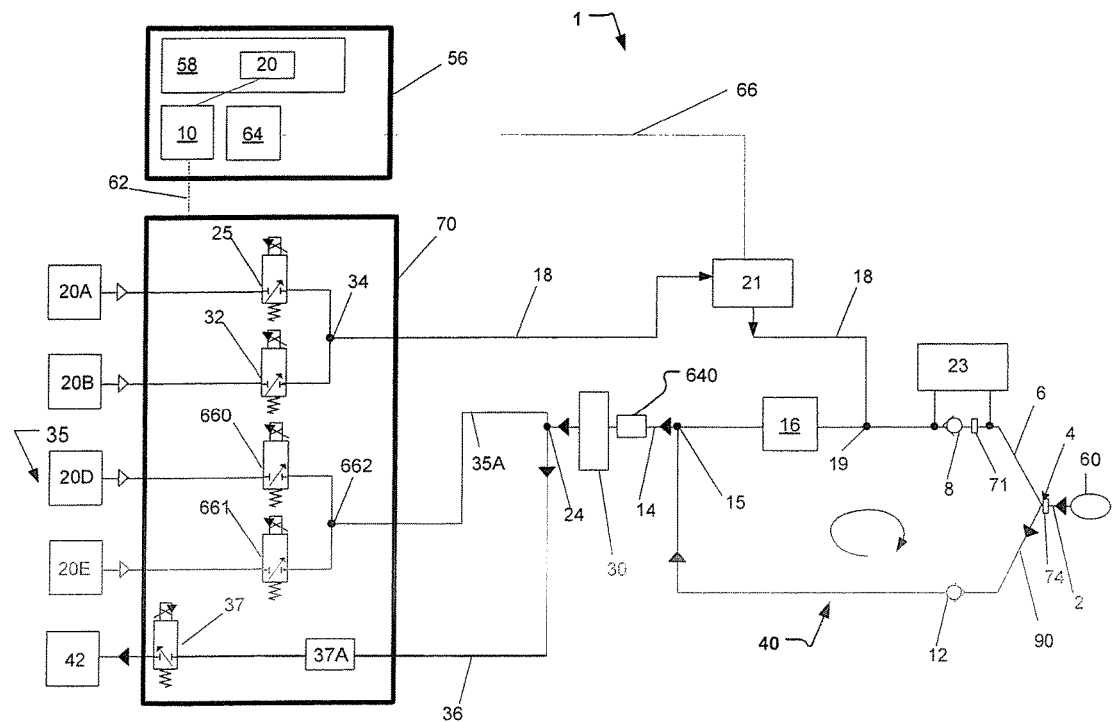
FIG. 4 is a schematic illustration of an anesthetic breathing apparatus having an anesthetic reflector unit, in an expiration phase.
Figure 5:
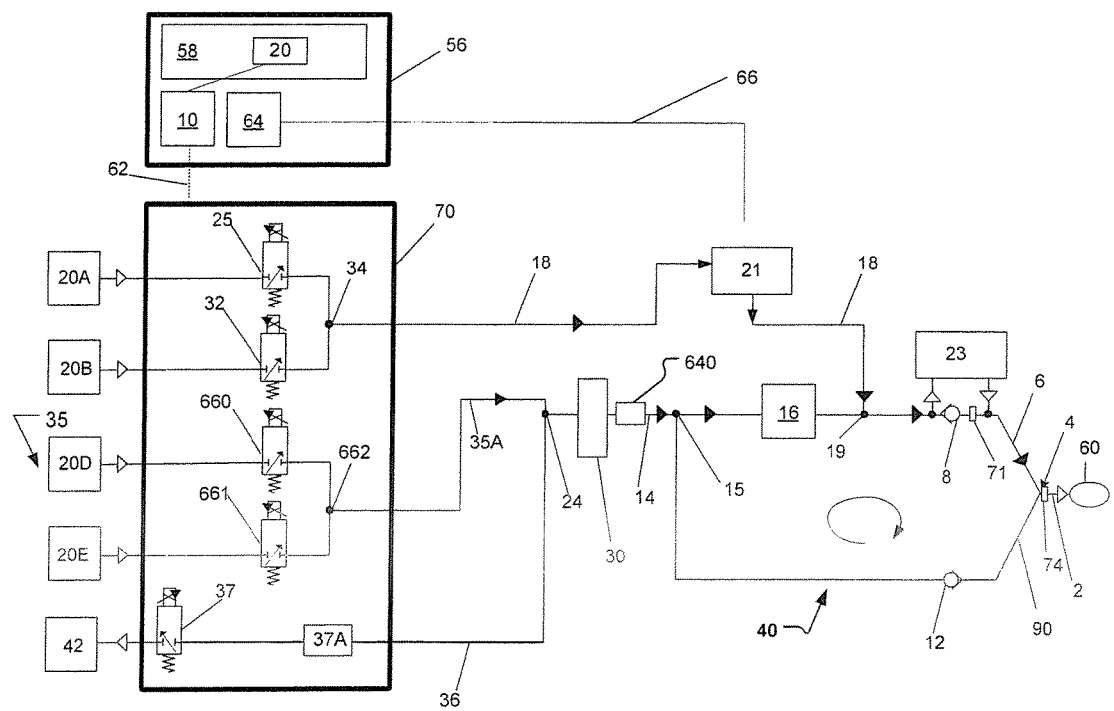
FIG. 5 is a schematic illustration of an anesthetic breathing apparatus having an anesthetic reflector unit, in an inspiration phase.

Now turning to FIGS. 4 and 5, the anesthesia system 1 illustrated schematically in FIG. 1 is described in more detail for providing a thorough understanding of the examples of the status indicator 50 and the underlying operation of the system 1.

FIG. 4 is a schematic illustration of an anesthetic breathing apparatus having an anesthetic reflector unit 30, in an expiration phase. In the anesthetic breathing apparatus the breathing circuit 40 s coupled with a mechanical ventilation system 70.

The airways of a patient 60 are connected to a patient tube 2 of a Y-piece 4 in a circular tubing system with an inspiration tube 6 and an expiration tube 90 provided with one-way valves 8, 12. A patient gas flow sensor and optionally a patient pressure sensor 74 or sample point for a pressure sensor is provided in the patient tube 2 connected to the Y-piece 4. Downstream the one-way valve 12, in FIG. 4 in a clockwise direction along the breathing circuit 40, a common expiration and inspiration line 14 is provided for the delivery of inspiration gas to the patient and evacuation of expiration gas from the patient. The common expiration and inspiration line 14 is coupled to the breathing circuit 40 at a junction 15. Further along the breathing circuit 40, the tubing passes through a $CO_2$ absorber 16 for removing $CO_2$ expired from the patient 60, in turn to be replaced with $O_2$ from FG via line 18.

Downstream the $CO_2$ absorber 16 the fresh gas supply branch line 18 is provided to feed gas into the breathing circuit 40 from a gas source. The fresh gas supply branch line 18 has a proximal portion in which fresh gas is supplied to an anesthetic vaporizer 21. The fresh gas is further conveyed via a distal portion of the fresh gas supply branch line 18, as desired enriched with gaseous anesthetic agent by the anesthetic vaporizer 21. The fresh gas supply branch line 18 is distally coupled to the breathing circuit 40 at a junction 19.

The common expiration and inspiration line 14 is provided with the volume reflector unit 30.

The fresh gas inhalation source may comprise multiple gas sources, such as an oxygen gas source 20A, and an air gas source 20B, as illustrated in FIG. 4. Additionally, the fresh inhalation gas source may comprise a nitrous oxide gas source (not shown).

The anesthetic vaporizer 21 is fluidly connected to the fresh gas supply branch line 18 downstream the multiple gas sources and upstream the junction 19.

A gas analyzer 23 is provided to analyze gas contents with an input of sample inspiratory gas in a side stream configuration. The side stream may be tapped downstream the junction 19 and upstream one-way valve 8 in the inspiratory branch. Alternatively, or in addition other and/or several sampling points for such side stream flow may be provided, such as at the Y-piece and/or at an expiratory branch or channel of the breathing circuit. A pressure sensor 71 may be provided between the first one-way valve 8 and the recirculation point of the sample gas.

At the side illustrated as turned opposite the patient in the breathing circuit 40, the volume reflector 30 of the common expiration and inspiration line 14 is coupled at a junction 24 to a reflector driving gas line 35A for pushing reflector driving gas into the proximal end of the volume reflector from a source of driving gas 35. Thus gas may be pushed out of the distal end of the volume reflector into the common expiration and inspiration line 14 downstream the volume reflector 30 and into the breathing circuit 40 towards the patient.

During inhalation, as illustrated in FIG. 5, a gas flow ratio may thus be controlled between the fresh gas line 18 and the line 14 in order to adjust a degree of rebreathing gas being pushed from volume reflector 30 via line 14 into the breathing circuit 7. This is how the RBF is adjusted, which may be graphically illustrated in a component of the status indicator 50.

Oxygen gas source 20A is coupled to an O2 inspiratory valve 25 that in its turn is connected to the fresh gas line 18 at a blender 34. Similarly, air gas source 20B is coupled to an air inspiratory valve 32 that also is coupled to the fresh gas line 18 at the blender 34. The O2 inspiratory valve 25 and the air inspiratory valve 32 are devised for adjusting the inlet flow and the proportions of the respective gases into the fresh gas line 18 prior to adding anesthetic agent in vaporizer 21.

A ventilation control system 56 may comprise a user input/output interface 58 with command input means and display means 20 for providing the status indicator 50.

Also, the ventilation control system 56 may comprise processing unit 10 for controlling mechanical ventilation system 70 and its components via a symbolically shown control line 62. The processing unit 10 enables vent of breathing gas from the mechanical ventilation system according to a set of predetermined control rules for controlling the expiratory valve 37 in accordance with ventilation mode requirements. Alternatively, or in addition to processing unit 10 other processing units (not shown) may provide the functions described herein in a distributed manner. The expiratory valve 37 is usually closed during inspiration and controls the expiratory pressure level, and expiratory flow, during expiration.

The processing unit 10 may be adapted to detect a reflector driving gas (RDG) crossing over the volume reflector unit 30 during inspiration based on the at least one property of the gas stream measured by a gas sensor unit 640. For instance, the gas sensor unit 640 may include a unit that measures a gas flow and/or identifies a gas composition of the gas flowing by, such as an ultrasound based gas sensor unit capable of both measuring gas flow and composition. In this manner, detection of RDG is provided as RDG composition is different from breathing gas composition. The processing unit 10 is further is adapted to set operational modes of said apparatus. Thus the processing unit 10 provides for controlled admixture of reflector driving gas (RDG) into the breathing circuit 40.

The ventilation control system 56 further comprises an anesthetic agent control unit 64. The anesthetic agent control unit 64 is devised to control the anesthetic vaporizer 21 via the symbolically shown control line 66 to control a desired composition of the FG for providing a desired patient gas composition, preferably mixed with re-breathed gas from the VR 60 for providing the RBF, during inspiration to patient 60.

An evacuation line or exhaust 36 is connected to the common expiration and inspiration line 14 and to the reflector driving gas line 35A at the junction 24. The evacuation line 36 leads, via a flow meter 37A and a pressure sensor to an expiratory valve 37 that is devised to control output of evacuated gas flow from the breathing circuit 40 via the VR 30 to a scavenging system 42 or to the atmosphere.

Gas sources 20A,B,D,E provide the ventilation system 70 with air and O2. Nitrous Oxide could also be provided (not shown). The gas is distributed via gas modules 25, 32, 660 661, inspiratory valves with integrated flow meters (not shown), to the blender junctions 34, 662. Oxygen, air and Nitrous Oxide, or a desired mixture thereof, is further conveyed to the vaporizer 21 providing fresh gas (FG) via FG-line 18, and oxygen and air to breathing circuit providing reflector driving gas (RDG) via RDG line 35A. Optionally only oxygen is provided as RDG.

The flow delivered to the patient during inspiration is thus defined by the sum of gas provided by the reflector driving gas line 35A and the fresh gas line 18.

Thus, the inspiratory valves may be actuated to a variety of flow selection modes where an arbitrary ratio may be adjusted between the reflector driving gas line 35A and the fresh gas line 18 by controlling the inspiratory valves 25, 32, 660, 661 in desired manner. Thus, the re-breathing fraction (RBF) may be adjustable in this manner by controlling the inspiratory valves.

The distribution of the amounts of gas flow between the fresh gas line 18 and the reflector driving gas line 35A is adjustable in real time by processing unit 10.

For instance by distributing the entire flow of gas from junction 34 to the fresh gas line 18, the re-breathing fraction (RBF) is zero, i.e. the entire flow of inspiratory gas into patient 60 originates from this line 18, including an addition of one or more anesthetic agents from vaporizer 21.

In order to increase the RBF, a portion of the flow of gas from junction 34 may instead provided via line 14, provided from pushing gas from volume reflector 30 into the breathing circuit towards the patient, by suitably controlling the gas flow in reflector driving gas line 35A, see FIG. 5. The gas pushed out of the volume reflector 30 by RDG controlled by the valves 660, 661, may thus be blended with gas originating from the fresh gas line 18 at junction 19 and further conveyed into the patient 1. The gas pushed from the volume reflector and/or adsorption filter 30 into the breathing circuit 7 is composed of previously exhaled patient gas, e.g. including one or more anesthetic agents. Hence, this previously exhaled patient gas is provided for re-breathing to the patient, after passing through the CO2 absorber 16. In a low flow operational mode (i.e. the highest possible RBF), the breathing apparatus may be controlled in such a manner that only the anesthetic agent and oxygen consumed by the patient (patient uptake) is re-added to the breathing circuit 40. Any leakage present may also be compensated for by increasing FG flow for re-addition of a leaked gas volume.

The gas flow during the expiratory phase is illustrated by the bold arrows on gas flow lines in FIG. 4. During expiration, the expiratory valve 37 is controlled to release gas to the evacuation 42. Exhalation gas from the patient 60 passes through the expiratory part of the breathing circuit 40 and via junction 15 into the line 14 and volume reflector 30. The expiratory flow is measured by the gas flow meter (gas sensor unit 640) in line 14. Expiratory gas enriched with exhaled anesthetic agent is pushed into the volume reflector 30. The RDG from the previous inhalation present in the volume reflector is pushed towards the expiratory valve 37 and further to evacuation 42. Expiratory pressure, e.g. for a positive end expiratory pressure (PEEP) regulation is provided by a pressure sensor, that may be integrated with flow meter 37A. Gas sensor unit 640 may provide for the expiratory flow information.

In practice very often a portion of the exhaled gas is lost by leakage, e.g. passing a cuff of patient tube 2 intubated into the trachea of the patient 1. Such leakage volume has to be compensated for during the next inspiration phase. Hence, the volume reflector is not filled with the entire exhaled volume (leakage volume is lost).

Leakage is thus a loss related to the patient side in the present context. The term leakage may in some examples include patient uptake.

FIG. 5 is a schematic illustration of an anesthetic breathing apparatus having an anesthetic reflector unit, in an inspiration phase.

In case no fresh gas is supplied via fresh gas line 18 to the breathing circuit 40 at junction 19, all inspiration volume is provided via the volume reflector 30 and common line 14 to junction 15, and further to the patient via carbon dioxide absorber 16. Leakage volume is calculated as (inspiration volume provided during the present inhalation phase minus expiration volume measured entering the volume reflector during the previous exhalation phase. Hence, a leakage volume is based on a difference of an inspiratory gas volume measured by said gas senor unit 640 comprising a volume leaving said reflector unit 30 during inspiration and a volume entering said reflector unit 30 during the preceding expiration. The leakage is provided for inclusion in the status indicator 50.

The entire inspiratory gas volume may also comprise a known portion delivered via the fresh gas line 18. In case a certain portion of the inspiration volume is provided via the fresh gas line 18, this volume is known from gas modules 25, 32, when these have integrated flow sensors. The entire inspiration volume is known when integrated flow sensors are provided in gas modules 660, 661.

It should be noted that data from measurement units is not simply taken and displayed as status indicators 50, but has a technical character, it is much more than merely conveying cognitive or aesthetic content directly to a human. As for instance describe above with reference to FIGS. 4 and 5, multiple sensor data, such as gas pressures, gas flows, gas compositions at multiple points in the anesthesia system is provided to the processing unit 10. Input data is for instance based on signals received by processing unit 10, or data sent to the latter, from e.g. flow meter 37A, gas sensor unit 640, gas flow sensor and/or patient pressure sensor 74, etc. Based on this input data, processing unit 10 calculates output data in a complex manner for providing the output of one or more components of a status indicator 50 on a display 20. Output data includes for instance the RBF, leakage, position of gas columns in a VR, etc. as described in detail herein. The processing unit 10 is configured to determine and communicate with said display so that at least one graphical representation element, based on said input data and/or output data, is provided on the display 20.

Figure 6:
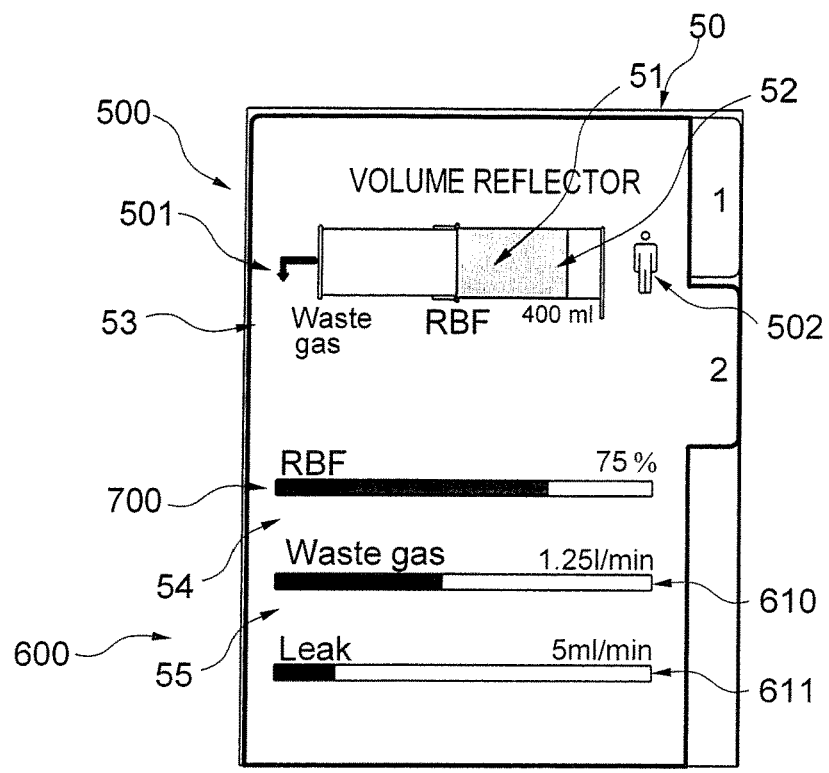
FIGS. 6, 7, 8A and B, 9, 10, 11 and 12 are schematic illustration of further examples of a various VRIs.
Figure 7:
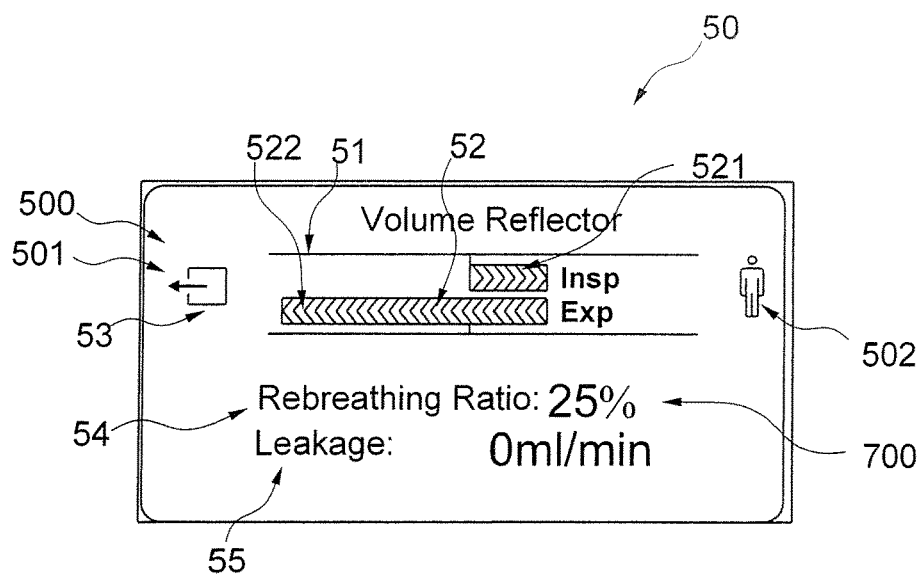
Figure 8A:
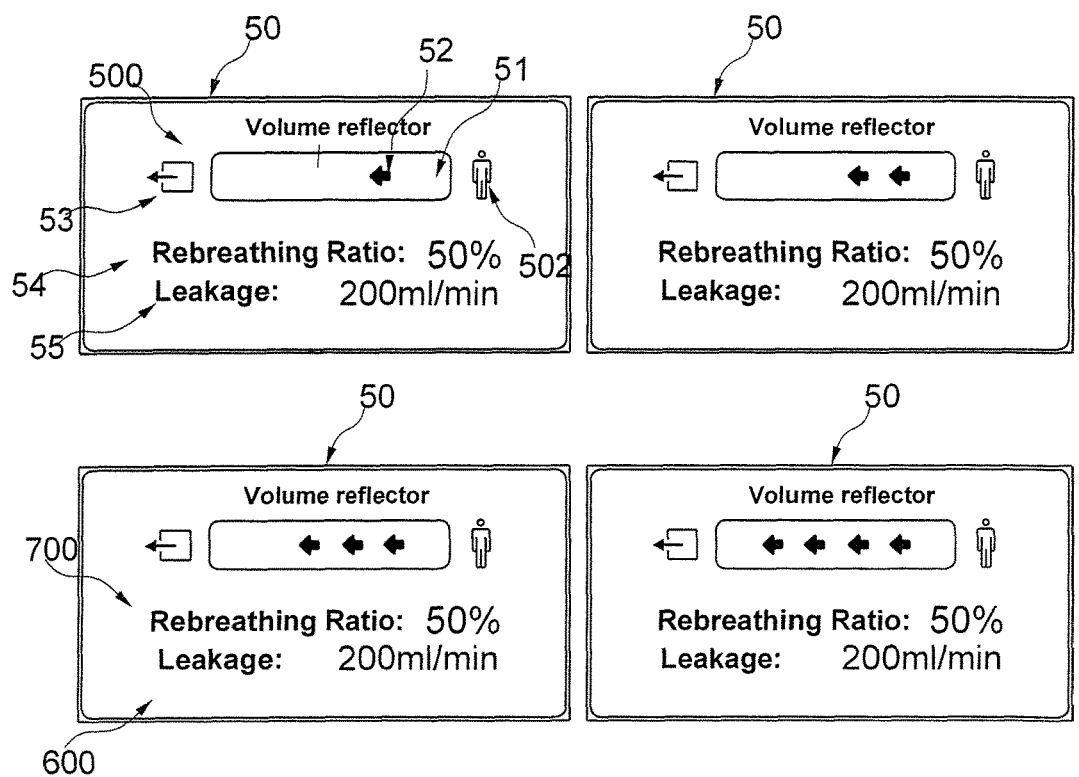

FIGS. 6, 7, 8A and B, 9, 10, 11 and 12 are schematic illustration of further examples of a various status indicators 50.

In FIG. 6 an alternative example of a status indicator 50 is illustrated. This example has an alternative layout for presenting a status indicator 50 than previous examples. For instance the Evac symbol 501 is different, which might be present in other examples too (not shown). Further, the balance indicator 600 has two separate bar graphs, namely one bar 610 for indicating waste gas flow and a second bar 611 for leakage flow.

The RBF is in the illustrated operative status 75%, which is due to the fact that there is some leakage and waste gas flow that is related to a corresponding fresh gas flow mixing with patient gas for re-breathing. This reduces the RBF.

The example in FIG. 6 may be regarded as an example of a system 1 that is being run economically, since little waste volume leaves through EVAC.

In FIG. 7 an alternative example of a status indicator 50 is illustrated. This example has an alternative layout for presenting a status indicator 50 than previous examples. A first 521 column represents the inspiration and the volume leaving the reflector 30 pushed by the RDG towards the patient 60. A second column 522 represents the expiration flow and the volume returning into the reflector during expiration. The second column 522 column starts from where the first column 521 ends. In the example it is illustrated that the second column 522 does travel further back during expiration than it has traveled during inspiration, i.e. more gas volume enters the VR from the breathing circuit during each expiration than has left the VR to the breathing circuit at the previous inspiration of the same breath. This means that with each expiration waste gas is sent to Evac from the VR. As leakage in the example is illustrated as 0 ml/min (no leakage) and the second column is approximately 4 times as large as the first column, the RBF is 25%, as illustrated. This illustration is an example of a system 1 that is being run uneconomically, since a large volume goes out through EVAC with every breathing cycle. Valuable anesthetic agent that could be re-breathed is wasted.

Figure 8B:
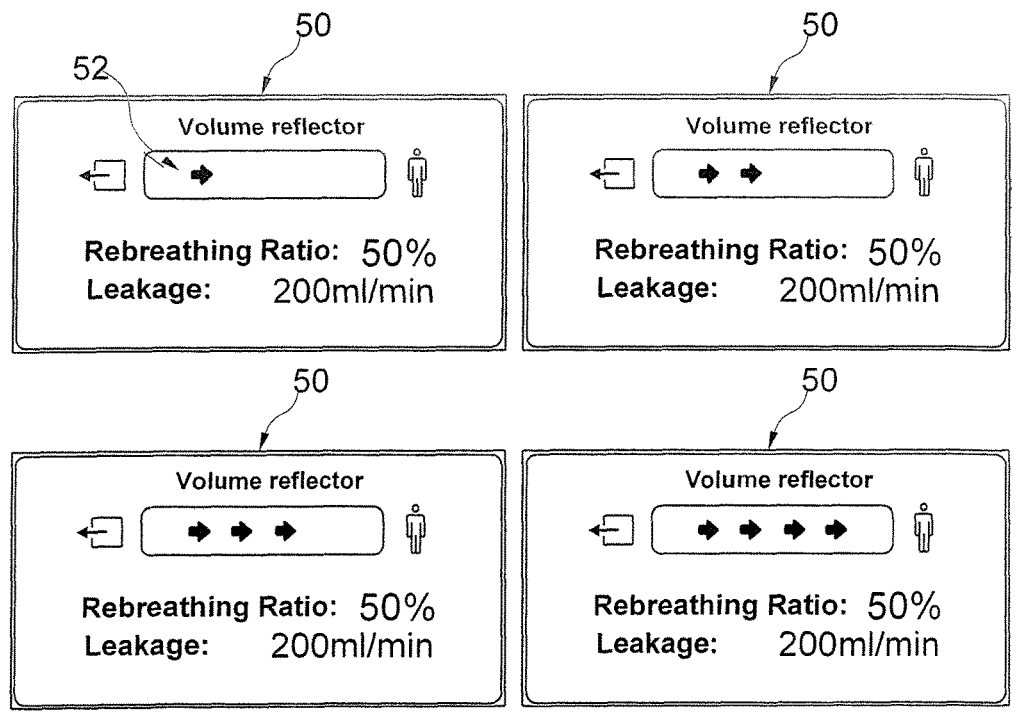

In FIGS. 8A and 8B an alternative example of a status indicator 50 is illustrated. This example has an alternative layout for presenting a status indicator 50 than previous examples. The graphical representation 51 of an extent of a driving gas of the volume reflector 30 and/or a patient gas in the volume reflector 30, and a graphical representation 52 of a flow of gas and a direction of the flow in the volume reflector 30, is provided with a series of arrows. This can be followed during expiration when patient gas enters the VR by the arrows increasing in number from right to left in FIG. 8A. In FIG. 8B, the inspiratory phase is illustrated by arrows moving in the opposite direction, from left to right. The RBF is 50% and there is a leakage of 200 ml/min illustrated as an example.

Figure 9:
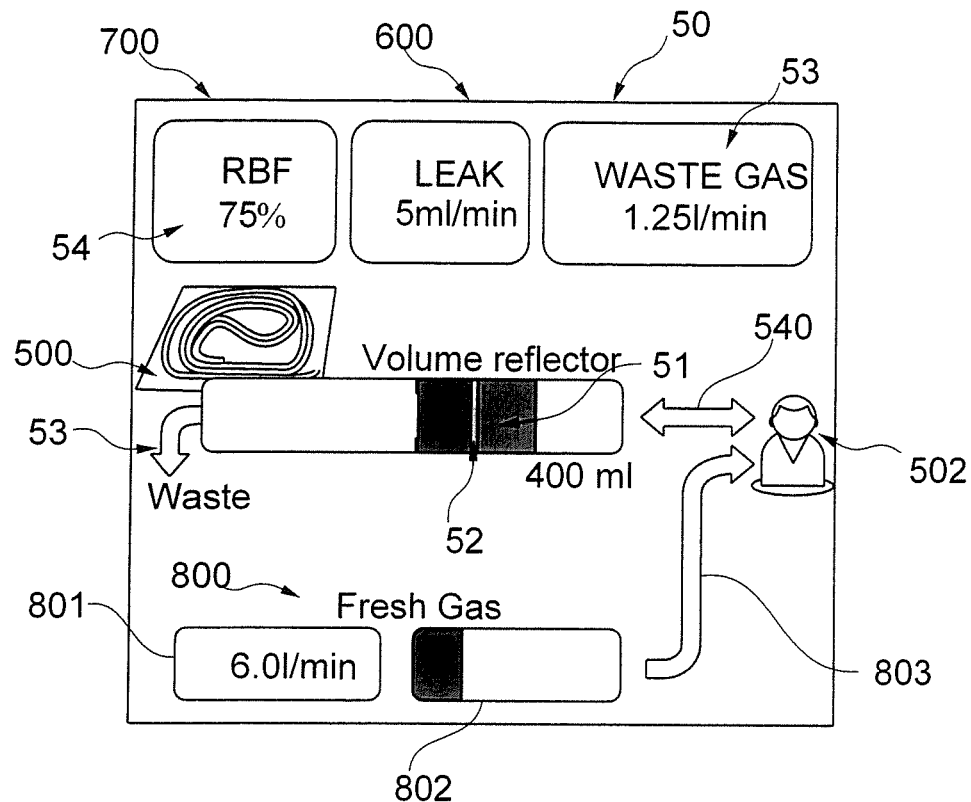

In FIG. 9 an alternative example of a status indicator 50 is illustrated. This example has an alternative layout for presenting a status indicator 50 than previous examples.

This example includes a fresh gas indicator 800. The fresh gas indicator 800 is a graphical representation of the FG flow into the breathing circuit 40. The fresh gas indicator 800 includes a metric 801, here having the exemplary value of 6.0 l/min. The fresh gas indicator 800 includes a bar graph 802 allowing for a quick understanding of the supplied FG level. The bar graph may have different colors for example for different gas compositions, anesthetic agents, or if below or above a threshold. Color coding thus may allow for the user to quickly identify for instance the components of the gas composition in the FG (N2O, Air, Anesthetic Agent etc.). Color coding thus may allow for the user to quickly identify a present range of the FG flow (low, normal, excessive) indicating economical or uneconomical operation of the system 1.

An arrow 803 illustrates the delivery of FG to the patient 502. An arrow 540 illustrates bi-directional gas communication with the reflector.

The example of FIG. 9 includes a graphical element identifying the physical appearance of the VR in system 1. Here, an image of a VR cassette is provided in the example. This allows the operator to quickly identify the VR status indicator. As in other examples, labels are provided at the respective elements of the status indicator 50, like "Volume Reflector", "Waste", etc.

Figure 10:
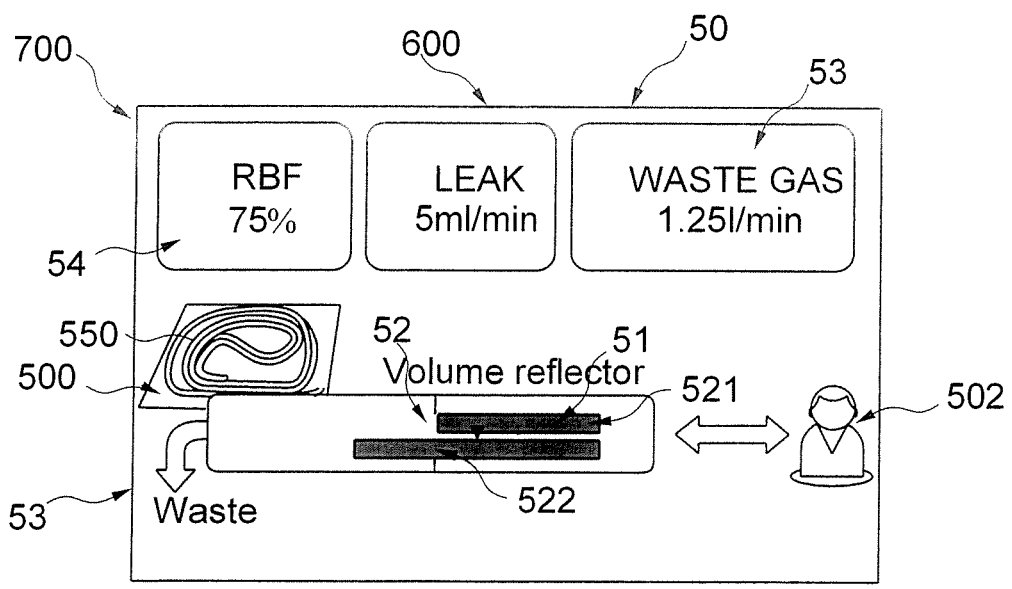

In FIG. 10 an alternative example of a status indicator 50 is illustrated. This example has an alternative layout for presenting a status indicator 50 than previous examples. This example is similar to the example of FIG. 9 without the fresh gas indicator. Similar to FIG. 7, the example of FIG. 10 includes a first 521 column which represents the inspiration and the volume leaving the reflector 30 pushed by the RDG towards the patient 60. A second column 522 represents the expiration flow and the volume returning into the reflector during expiration, see further above referring to the like elements in FIG. 9.

Figure 11:
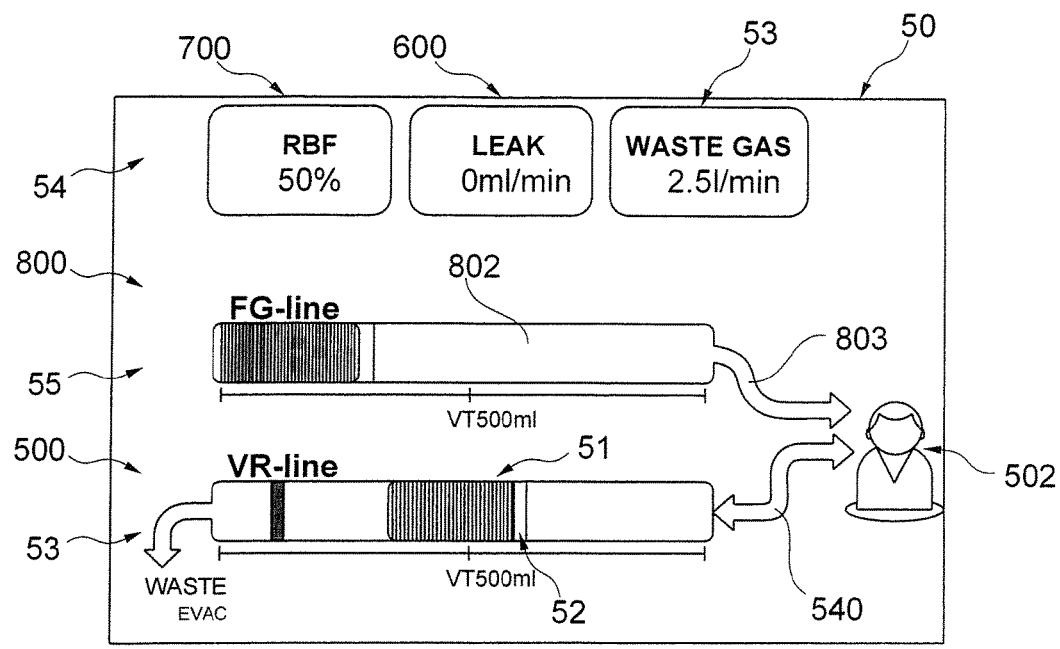
Figure 12:
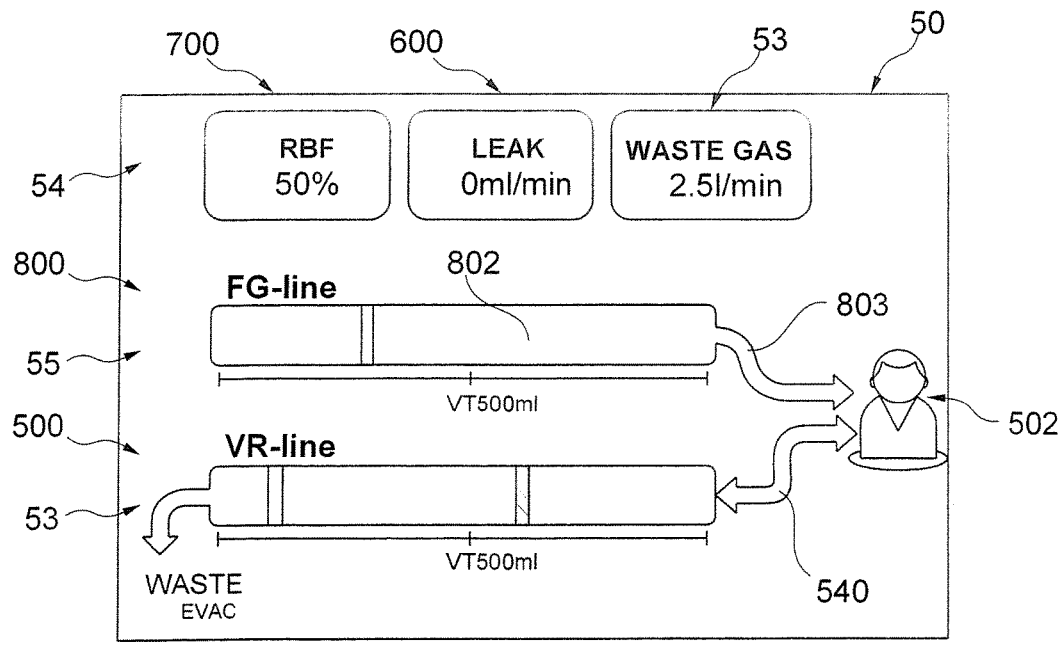

In FIGS. 11 and 12 an alternative example of a status indicator 50 is illustrated. This example has an alternative layout for presenting a status indicator 50 than previous examples. FIG. 11 represents the inspiratory phase and FIG. 12 represents the expiratory phase. This example, like others, for instance that of FIG. 9, illustrates the gas flows in the VR, breathing circuit, to and from the patient in a very illustrative manner allowing the operator to comprehensively understand the operation and status of the system 1.

Figure 13:
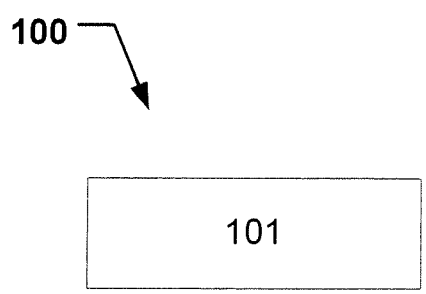
FIG. 13 is a flowchart of a method.

FIG. 13 is a flowchart of a method 100 for providing a status indicator 50 for a volume reflector 30 and/or breathing circuit 40 on a display 20 of an anesthesia system 1. The anesthesia system 1 includes a processing unit 10 for providing the status indicator 50 on the display 20. The method includes providing 101 the status indicator 50 with a graphical representation of
- an extent of a driving gas of the volume reflector 30 and/or a patient gas in the volume reflector 30, and/or
- a flow of gas and a direction of the flow in the volume reflector 30, and/or
- a waste gas flow out of the volume reflector 30 relative a fresh gas flow in the system 1, and/or
- a re-breathing fraction (RBF), and/or
- a balance between the fresh gas flow and patient uptake and/or leakage of gas from the breathing circuit.

Figure 14:
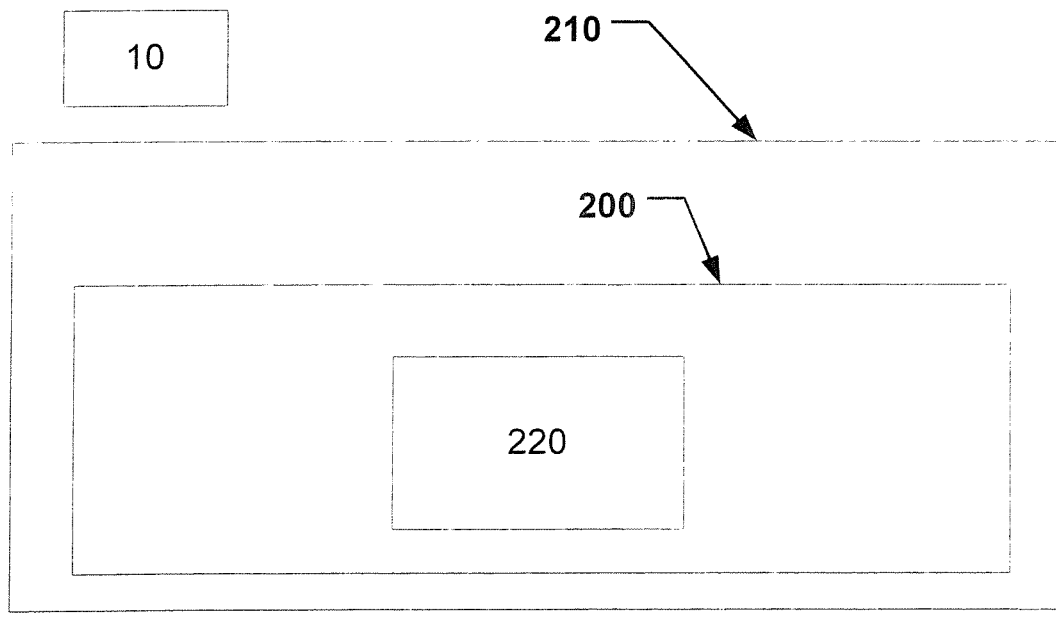
FIG. 14 is a schematic illustration of a computer program.

FIG. 14 is a schematic illustration of a computer program 200, which is stored on a computer readable medium 210, for processing by a processing unit 10 of an anesthesia system 1. The computer program 200 comprises code segments 220 for providing a status indicator 50 for a volume reflector 30 and/or breathing circuit 40 on a display 20 of an anesthesia system 1. The anesthesia system 1 includes a processing unit 10 for providing the status indicator 50 on the display 20. The computer program includes code segments 220 for providing the status indicator 50 with a graphical representation of
- an extent of a driving gas of the volume reflector 30 and/or a patient gas in the volume reflector 30, and/or
- a flow of gas and a direction of the flow in the volume reflector 30, and/or
- a waste gas flow out of the volume reflector 30 relative a fresh gas flow in the system 1, and/or
- a re-breathing fraction (RBF), and/or
- a balance between the fresh gas flow and patient uptake and/or leakage of gas from the breathing circuit.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

We claim as our invention:

1. An anesthesia system having a volume reflector, a breathing circuit, a processing unit, and a display operatively connected to said processing unit, wherein said processing unit is configured to provide a status indicator on said display for gas in said volume reflector, said status indicator including a real-time graphical representation
   - of a driving gas of said volume reflector and a patient gas in said volume reflector; and
   - a flow of gas and a direction of said flow in said volume reflector;
   - wherein said status indicator comprises a graphical representation of adjacent gas pillars representing said driving gas and said patient gas in operation in said volume reflector, and said graphical representation further includes a representation of a present extent of said driving gas pillar and said patient gas pillar in said volume reflector during both an inhalation and an exhalation of a breathing cycle.

2. The system of claim 1, wherein said graphical representation includes at least one of a representation of a present wave front position and direction of said driving gas pillar adjacent said patient gas pillar in said volume reflector.

3. The system of claim 2, wherein said graphical representation further includes a mid line, and said processing unit is configured to zero said presented wave front position to a zero position, at said mid line, at an inspiratory end prior to a subsequent expiration.

4. The system of claim 2, wherein said processing unit is configured to zero said presented wave front position to said zero position upon at least one of each new inspiration start for determining said waste gas flow, and a penetration of driving gas into said breathing circuit for each individual breath.

5. The system of claim 1, wherein said processing unit is configured to integrate said gas flow in said volume reflector over time and to determine a drift in said wave front position over time, wherein said drift is provideable in said graphical representation.

6. The system of claim 1, wherein said graphical representation of said flow of gas and said direction of said flow in said volume reflector includes a flow indicator for indicating a current gas flow and its direction in or out of the volume reflector during a breathing cycle.

7. The system of claim 6, wherein said status indicator for said volume reflector includes a graphical representation of a net accumulated volume of gas entering and leaving said volume reflector through at least one of a first port and a second port, during an expiration and a subsequent inspiration of ventilation.

8. The system of claim 7, wherein a penetration of said driving gas into said breathing circuit is determinable from said status indicator.

9. The system of claim 8, wherein said status indicator further includes a leakage rate indicator.

10. The system of claim 1, wherein said status indicator further includes a graphical representation of said waste gas flow to an exhaust of said system.

11. The system of claim 1, wherein said processing unit is configured to provide at least a part of said status indicator with different visually identifiable entities for differentiating between economically beneficial or disadvantageous operation of said volume reflector with regard to re-breathing of anesthetic gas components from said volume reflector.

12. The system of claim 1, wherein
   said breathing circuit is configured to ventilate a patient with inspiration gas and receiving patient gas during exhalation from said patient when connected to said breathing circuit, said volume reflector has a fixed volume, a first port, and a second port, wherein said breathing circuit is fluidly connected to said first port, such that said patient gas is receivable during expiration via said first port while gas in said volume reflector is pushed through said second port as said waste gas flow to an exhaust of said anesthesia system, and such that a flow of gas from said volume reflector is provided to said breathing circuit during inspiration, wherein expired gas from a preceding expiration is re-breathable by said patient in subsequent inspiration from said volume reflector, and said system including;

a source of driving gas fluidly connected to said second port for pushing said gas from said volume reflector into said breathing circuit during inspiration, and a source of fresh gas for delivery of a fresh gas flow mixable with said gas pushed from said volume reflector to said patient during inspiration, wherein said re-breathing fraction (RBF) is obtainable as a portion of said re-breathed gas in said inspiration gas.

13. The anesthesia system of claim 1, wherein the processing unit is configured to provide a graphical indicator for fresh gas economy in said anesthesia system on a display of said system, said graphical fresh gas economy indicator including a waste gas flow out of said volume reflector relative a fresh gas flow into said system, and a re-breathing fraction (RBF), for indicating a balance between fresh gas flow and patient uptake plus leakage from said system.

14. The anesthesia system of claim 1, wherein the processing unit is configured to provide a graphical indicator for fresh gas economy in said anesthesia system on a display of said system, said graphical fresh gas economy indicator including a graphical representation of a fresh gas flow minus patient uptake and leakage from said system, or a graphical representation of a quotient of re-breathed gas to a fresh gas portion in inspired gas.

15. The system of claim 1, wherein the status indicator further includes a graphical representation of at least one of:

a waste gas flow out of said volume reflector relative a fresh gas flow in said system;

a re-breathing fraction (RBF); and a balance between said fresh gas flow and patient uptake, between said fresh gas flow and patient uptake and leakage of gas from said breathing circuit or between said fresh gas flow and leakage of gas from said breathing circuit.

16. A method of providing a status indicator for a volume reflector and/or breathing circuit on a display of an anesthesia system, said anesthesia system including a processing unit for providing said status indicator on said display, wherein said method includes providing said status indicator with a real-time graphical representation of:

an extent of a driving gas of said volume reflector and a patient gas in said volume reflector; and a flow of gas and a direction of said flow in said volume reflector;

wherein said status indicator comprises a graphical representation of adjacent gas pillars representing said driving gas and said patient gas in operation in said volume reflector, and said graphical representation further includes a representation of a present extent of said driving gas pillar and said patient gas pillar in said volume reflector during both an inhalation and an exhalation of a breathing cycle.

17. A computer program stored on a computer readable medium, for processing by a processing unit of an anesthesia system, said computer program comprising code segments for providing a status indicator for a volume reflector and/or breathing circuit on a display of an anesthesia system, said anesthesia system including a processing unit for providing said status indicator on said display, wherein said computer program includes code segments for providing said status indicator with real-time graphical representation of:

an extent of a driving gas of said volume reflector and a patient gas in said volume reflector; and a flow of gas and a direction of said flow in said volume reflector;

wherein said status indicator comprises a graphical representation of adjacent gas pillars representing said driving gas and said patient gas in operation in said volume reflector, and said graphical representation further includes a representation of a present extent of said driving gas pillar and said patient gas pillar in said volume reflector during both an inhalation and an exhalation of a breathing cycle.

18. An anesthesia system including a volume reflector of fixed volume connected to a breathing circuit of said system at a first port and connected at a second port to a source of driving gas as well as an exhaust of said system, said system including an efficiency meter including a first indicator for a status of said volume reflector including:

an extent of a driving gas of said volume reflector and a patient gas in said volume reflector; and a flow of gas and a direction of said flow in said volume reflector;

wherein said status indicator comprises a real-time graphical representation of adjacent gas pillars representing said driving gas and said patient gas in operation in said volume reflector, and said graphical representation further includes a representation of a present extent of said driving gas pillar and said patient gas pillar in said volume reflector during both an inhalation and an exhalation of a breathing cycle.

19. An anesthesia system having a processing unit, a display operatively connected to said processing unit, and a volume reflector connected to a breathing circuit of said system at a first port and connected at a second port to a source of driving gas as well as an exhaust of said system, wherein said processing unit is configured to determine and communicate to said display at least one of:

an extent of a driving gas of said volume reflector and a patient gas in said volume reflector; and a flow of gas and a direction of said flow in said volume reflector;

wherein said status indicator comprises a real-time graphical representation of adjacent gas pillars representing said driving gas and said patient gas in operation in said volume reflector, and said graphical representation further includes a representation of a present extent of said driving gas pillar and said patient gas pillar in said volume reflector during both an inhalation and an exhalation of a breathing cycle, and wherein a clinical decision support system is provided in said anesthesia system for facilitating an operator of said system taking decisions related to adjustments of said fresh gas delivered to said breathing circuit and setting said re-breathing fraction.

\* \* \* \* \*